US012594319B2

(12) United States Patent
Coates et al.

(10) Patent No.: US 12,594,319 B2
(45) Date of Patent: Apr. 7, 2026

(54) PHARMACEUTICAL DEVELOPMENT

(71) Applicant: HELPERBY THERAPEUTICS LIMITED, London (GB)

(72) Inventors: Professor Anthony Coates, London (GB); Yanmin Hu, London (GB)

(73) Assignee: HELPERBY THERAPEUTICS LIMITED, London (GB)

( * ) Notice: Subject to any disclaimer, the term of this patent is extended or adjusted under 35 U.S.C. 154(b) by 1000 days.

(21) Appl. No.: 17/630,645

(22) PCT Filed: Jul. 28, 2020

(86) PCT No.: PCT/GB2020/051810
§ 371 (c)(1),
(2) Date: Jan. 27, 2022

(87) PCT Pub. No.: WO2021/019234
PCT Pub. Date: Feb. 4, 2021

(65) Prior Publication Data
US 2022/0257699 A1 Aug. 18, 2022

(30) Foreign Application Priority Data

Jul. 29, 2019 (GB) ...................................... 1910787

(51) Int. Cl.
| | |
|---|---|
| A61K 9/00 | (2006.01) |
| A61K 9/08 | (2006.01) |
| A61K 9/19 | (2006.01) |
| A61K 31/7072 | (2006.01) |
| A61K 38/12 | (2006.01) |
| A61P 31/04 | (2006.01) |

(52) U.S. Cl.
CPC ................ *A61K 38/12* (2013.01); *A61K 9/08* (2013.01); *A61K 31/7072* (2013.01); *A61P 31/04* (2018.01)

(58) Field of Classification Search
CPC ...... A61K 38/12; A61K 9/08; A61K 31/7072; A61K 9/19; A61K 9/0019; A61P 31/04; Y02A 50/30
See application file for complete search history.

(56) References Cited

U.S. PATENT DOCUMENTS

2016/0030506 A1* 2/2016 Hu ............................. A61P 1/18
514/1.6

FOREIGN PATENT DOCUMENTS

| | | |
|---|---|---|
| CN | 101879145 A | 11/2010 |
| CN | 104043103 A | 9/2014 |
| WO | 2011051070 A1 | 5/2011 |
| WO | 2014147405 A1 | 9/2014 |
| WO | 2014195405 A1 | 12/2014 |
| WO | 2015114340 A1 | 8/2015 |
| WO | 2017098274 A1 | 6/2017 |
| WO | 2018172733 A1 | 9/2018 |
| WO | 2021019233 A1 | 2/2021 |

OTHER PUBLICATIONS

Ingle et al., "Pre-filled syringe—a ready-to-use drug delivery system: a review," Expert Opinion on Drug Delivery 11:1391-1399 (2014) (Year: 2014).*
Colistin, ChemSpider ID 4470591, accessed Apr. 13, 2025 at URL chemspider.com/Chemical-Structure.4470591.html (Year: 2025).*
Khandagale et al., "Lyophilization Technique: A Review," Asian J. Res. Pharm. Sci. 6(4): 269-276 (2016) (Year: 2016).*
Second Chinese Office Action, Application No. 202080068232.4, dated Sep. 29, 2024.
"National Pharmaceutical Secondary Vocational Education Pharmacy Planning Textbook: Pharmaceutical Commodity Science", Gan Youqing, p. 83, China Medical Science and Technology Press, 1st edition, May 2011, 5th printing, Feb. 2015.
"Pharmacopoeia of the People's Republic of China, 2010 Edition, Third Supplement", National Pharmacopoeia Commission, pp. 113-114, China Medical Science and Technology Press, Nov. 2014, 1st edition.
PCT International Search Report and Written Opinion, Application No. PCT/GB2020/051810, dated Nov. 4, 2020.
European Pharmacopoeia 9.4, Colistimethate Sodium, (Jul. 2017:0319), pp. 5356-5363.
Bai et al., "A Simple HPLC Method for the Separation of Colistimethate Sodium and Colistin Sulphate", Chromatography Separation Techniques, 2011, vol. 2, Issue 1, pp. 1-4.
Barnett et al., "Sodium Sulphomethyl Derivatives of Polymyxins", Brit. J. Pharmacol., 1964, vol. 23, Issue 3, p. 552-574.
Berge et al., "Pharmaceutical Salts" Journal of Pharmaceutical Sciences, 1977, vol. 66, No. 1, pp. 1-19.
Bergen et al., "Colisin Methanesulfonate is an Inactive Prodrug of Colistin against Pseudomonas aeruginosa", Antimicrobial Agents and Chemotherapy, 2006, vol. 50, No. 6, pp. 1953-1958.
Brink et al., "Multicomponent antibiotic substances produced by fermentation: Implications for regulatory authorities, critically ill patients and generics", International Journal of Antimicrobial Agents, 2013, pp. 1-7.
Dutkiewicz et al., "Water Activity in Aqueous Solutions of Homogeneous Electrolytes: The Effect of Ions on the Structure of Water", ChemPhysChem, 2002, vol. 3, No. 2, pp. 221-224.
Coates et al., "The Future Challenges Facing the Development of New Antimicrobial Drugs", Nature Reviews, Drug Discovery, 2002, vol. 1, pp. 895-912.
European Pharmacopoeia, "5.3. Statistical Analysis of Results of Biological Assays and Tests", pp. 571-600.
Herrmann et al., "Intracellular Activity of Zidovudine (3'-Azido-3'-Deoxythymidine, AZT) against *Salmonella typhimurium* in the Macrophage Cell Line J774-2", Antimicrobial Agents and Chemotherapy, 1992, vol. 36, No. 5, pp. 1081-1085.

(Continued)

*Primary Examiner* — Julie Ha
*Assistant Examiner* — Kristina M Hellman
(74) *Attorney, Agent, or Firm* — MacMillan, Sobanski & Todd, LLC

(57) ABSTRACT

The present invention relates to a pharmaceutical product in the form of a storage stable lyophilisate or a pharmaceutical formulation in the form of a sterile solution for parenteral administration. Both the lyophilisate and solution consist essentially of a polymyxin selected from polymyxin E, polymyxin B, or a pharmaceutically acceptable derivative thereof, and zidovudine or a pharmaceutically acceptable derivative thereof. The solution further includes an aqueous carrier.

19 Claims, 1 Drawing Sheet

(56) References Cited

OTHER PUBLICATIONS

Hu et al., "Azidothymidine Produces Synergistic Activity in Combination with Colistin against Antibiotic-Resistant Enterobacteriaceae", Antimicrobial Agents and Chemotherapy, 2018, vol. 63, Issue 1, pp. 1-11.

He et al., "Pharmacokinetics of four different brands of colistimethate and formed colistin in rats", Journal of Antimicrobial Chemotherapy, 2013, vol. 68, pp. 2311-2317.

Li et al., "Evaluation of Colistin as an agent against multi-resistant Gram-negative bacteria", International Journal of Antimicrobial Agents, 2005, pp. 11-25.

Li et al., "Colistin: the re-emerging antibiotic of multidrug-resistant Gram-negative bacterial infections", Lancet Infect. Dis., 2006, vol. 6, pp. 589-601.

Li et al., "Stability of Colistin and Colistin Methanesulfonate in Aqueous Media and Plasma as Determined by High-Performance Liquid Chromatography", Antimicrobial Agents and Chemotherapy, 2003, vol. 47, No. 4, pp. 1364-1370.

McMillan et al., "Sodium Colistimethate I: Dissociations of Aminomethanesulfonates in Aqueous Solution", Journal of Pharmaceutical Sciences, 1969, vol. 58, No. 6, pp. 730-737.

Mohamed et al., "Application of a Loading Dose of Colistin Methanesulfonate in Critically Ill Patients: Population Pharmacokinetics, Protein Binding, and Prediction of Bacterial Kill", Antimicrobial Agents and Chemotherapy, 2012, vol. 56, No. 8, pp. 4241-4249.

Remington, "The Science and Practice of Pharmacy", Lippincott Williams & Wilkins, 21st Edition, 2005.

Schiff, "Eine neue Rhihe organischer Diamine" Justus Liebigs Annalen der Chemie, 1866, vol. 140, pp. 92-137.

Wallace et al., "Self-assembly behaviour of colistin and its prodrug colistin methanesulfonate: implications for solution stability and solubilization", J Phys Chem B., 2010, vol. 114, No. 14, pp. 1-16.

Wallace et al., "Stability of Colistin Methanesulfonate in Pharmaceutical Products and Solution for Administration to Patients", Antimicrobial Agents and Chemotherapy, 2008, vol. 52, No. 9, pp. 3047-3051.

European Pharmacopoeia 9.0, Zidovudine (Jan. 2017:1059), pp. 3962-3964.

European Pharmacopoeia 9.4, Colistimethate Sodium, (Jul. 2017:0319), pp. 5354-5356.

European Pharmacopoeia 9.0, HPLC, 2.2.29, pp. 46-47.

European Pharmacopoeia 9.7, Microbiological Assay of Antibiotics, 2.7.2, pp. 6309-6314.

Lin et al., "Novel Polymyxin Combination with the Antiretroviral Zidovudine Exerts Synergistic Killing against NDM-Producing Multidrug-Resistant Klebsiella pneumoniae", Antimicrobial Agents and Chemotherapy, 2019, vol. 63, Issue 4, pp. 1-11.

European extended search report, dated Aug. 11, 2025, Application No. 25180290.6.

* cited by examiner

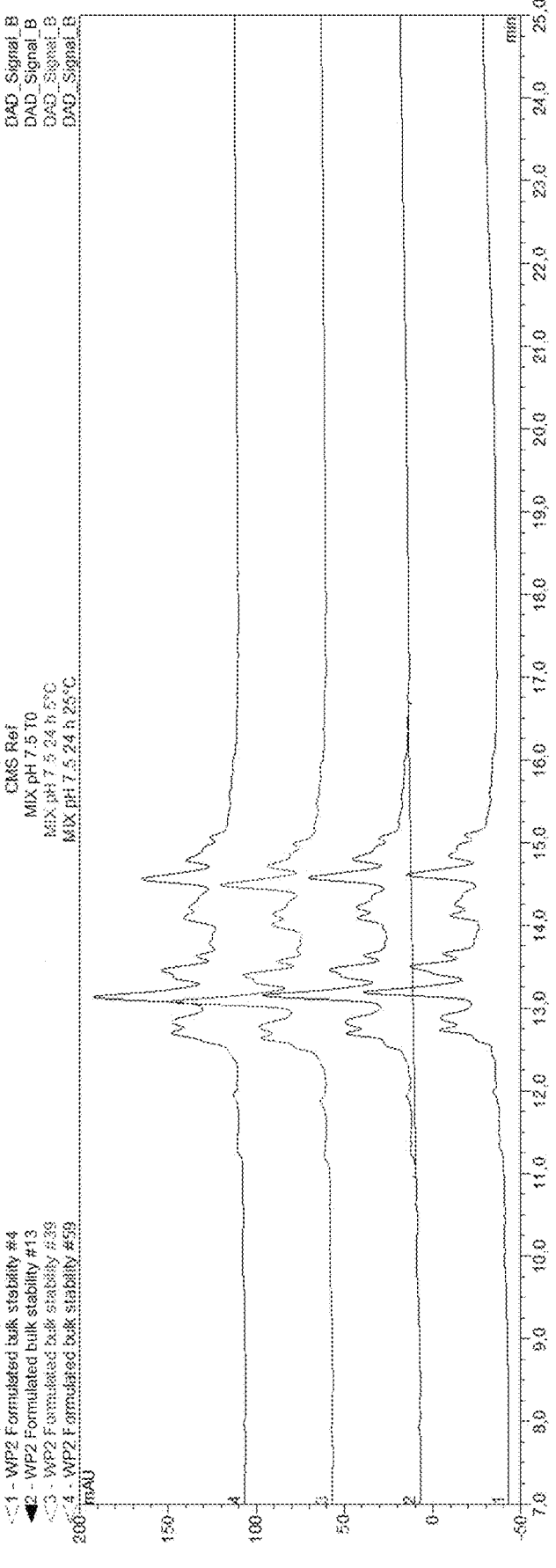

PHARMACEUTICAL DEVELOPMENT

This application is a national stage application of international application PCT/GB2020/051810, filed under the authority of the Patent Cooperation Treaty on Jul. 28, 2020, published; which claims priority to United Kingdom Application No. 1910787.9, filed on Jul. 29, 2019. The entire disclosure of each of the aforementioned applications is hereby incorporated herein by reference for all purposes.

FIELD OF THE INVENTION

The present invention relates to a pharmaceutical product in the form of a storage stable lyophilisate and a pharmaceutical formulation in the form of a sterile solution for parenteral administration. Both include a polymyxin and zidovudine, or pharmaceutically acceptable derivatives thereof, and may be useful in the treatment of Gram-negative bacterial infections, e.g. infections caused by *Enterobacteriaceae* or *Enterobacter*.

BACKGROUND TO THE INVENTION

The emergence of multi-drug resistant Gram-negative bacteria that cause nosocomial infections is a growing worldwide problem. Indeed, more than 70% of bacteria that give rise to hospital acquired infections in the USA resist at least one of the main antimicrobial agents that are typically used to fight infection (Nature Reviews, Drug Discovery, 1, 895-910 (2002)).

Such limited therapeutic options have led to an increased clinical use of colistin and polymyxin B, both polymyxin antibiotics developed over 50 years ago, because these compounds, unlike many other antimicrobial agents, have retained their activity against a number of multi-drug resistant pathogens. This is possibly due to limited clinical use; the parenteral formulation of colistin for example, quickly decreased in utilisation following authorisation in the 1960s due to the existence of other more suitable therapeutic options. Nevertheless, polymyxins are currently listed among the critically important antimicrobials and are attracting widespread interest and investigation.

Polymyxins are a group of naturally occurring multi-component cyclic polypeptide antibiotics produced by selected strains of the spore-forming soil bacterium *Paenibacillus polymyxa* (formally known as *Bacillus polymyxa* var. *colistinus*). Five major and chemically distinct members of the group have been recognised and are designated as polymyxins A, B, C, D and E, of which B and E are available commercially and approved in the US and Europe. Polymyxin B is approved for topical use and polymyxin E, usually referred to as colistin, is approved for oral, parenteral and inhalation use. Two forms of colistin are used clinically: colistin sulfate for oral administration and its prodrug, colistimethate sodium or CMS, for parenteral and inhalation use. Li et al., (Lancet Infect Dis. 2006 September; 6(9): 589-601) describes colistin as the "re-emerging antibiotic for multidrug-resistant Gram-negative bacterial infections".

Resistance to polymyxins is, however, on the rise and a growing body of evidence suggests that resistance to polymyxins can emerge with monotherapy. A solution to this problem is polymyxin combination therapy; such therapy has been demonstrated to improve bacterial killing and prevent the emergence of resistance. Hu et al., (Antimicrob Agents Chemother. 2018 Dec. 21; 63(1)) explains how azidothymidine produces synergistic activity in combination with colistin against antibiotic-resistant *Enterobacteriaceae*.

Azidothymine (AZT), also known as zidovudine, is a nucleoside analogue reverse-transcriptase inhibitor, a type of antiretroviral drug which is approved in the US and Europe for the treatment of HIV/AIDs infection. As well as its antiretroviral activity against HIV, the antibacterial effect of zidovudine has been demonstrated both in vitro and in vivo with experimental models of gram-negative bacteria infections (Hermann et al., Antimicrob Agents Chemther., 1992 May; 36(5): 1081-1085).

Synergy between a polymyxin and zidovudine was first discovered by the present inventors, and is described in the International Patent Application PCT/GB2014/050878 which published as WO 2014/147405 A1. Further experiments on the ratio of zidovudine to colistin were also carried out by the present inventors, and these are described in the International Patent Application PCT/GB2016/053901 which published as WO 2017/098274 A1.

There is, however, no disclosure or teaching in the art of how to prepare a pharmaceutical formulation or a medicinal product for successful parenteral administration of a therapeutically effective amount of a polymyxin in combination with a therapeutically effective amount of zidovudine. Each of these compounds is only commercially available as a monotherapy product, and whilst WO 2014/147405 A1 and WO 2017/098274 A1 disclose the combination per se along with the possibility of preparing a pharmaceutical composition containing the combination, there is no enabling disclosure in either of these prior applications of how to prepare a medicinal product containing the combination which can be used parenterally to administer therapeutically effective amounts of both compounds to a subject in need thereof. The focus in these prior disclosures is the synergy between the two actives in an in vitro environment. There is also no disclosure of an appropriately storage stable form of this combination which would allow the effective and reliable preparation of a solution for injection.

Commercial exploitation of the combination containing a polymyxin (e.g. colistin) and zidovudine thus requires the development of a formulation that is acceptable in terms of storage stability and ease of preparation. Because of the synergistic relationship between the two compounds, the formulation of an acceptable medicinal product or pharmaceutical formulation is not, however, straightforward and presents challenges not encountered when formulating individual compounds. In particular, it is not possible to predict how this relationship will impact the solubility of each compound in organic or other solvents and/or whether the product is storage stable.

It is an object of the present invention to provide a pharmaceutically useful preparation of a polymyxin and zidovudine, particularly one including, as the active ingredients, a polymyxin selected from polymyxin E, polymyxin B or a pharmaceutically acceptable derivative thereof, and zidovudine or a pharmaceutically acceptable derivative thereof.

SUMMARY OF THE INVENTION

In a first aspect the present invention provides a pharmaceutical product in the form of a lyophilisate, which lyophilisate consists essentially of a therapeutically effective amount of a polymyxin selected from polymyxin E, polymyxin B or a pharmaceutically acceptable derivative thereof, a therapeutically effective amount of zidovudine or a pharmaceutically acceptable derivative thereof, and optionally one or more buffering agent(s). The lyophilisate is storage stable, and may be stored in vials or cartridges ready for re-constitution with an aqueous carrier (e.g. water or a buffered aqueous solution) to form a sterile solution for parenteral administration.

In a second aspect the present invention thus provides a pharmaceutical formulation in the form of a sterile solution for parenteral administration, which solution consists essentially of a therapeutically effective amount of a polymyxin selected from polymyxin E, polymyxin B or a pharmaceutically acceptable derivative thereof, a therapeutically effective amount of zidovudine or a pharmaceutically acceptable derivative thereof, an aqueous carrier, and optionally one or more buffering agent(s).

The advantages of the first and second aspect include the preparation of a storage stable form of the combination which allows the effective and reliable preparation of a pharmaceutically useful formulation, namely the sterile solution ready for parenteral administration. The sterile solution is also storage stable, as discussed in more detail below.

In a third aspect the present invention provides the pharmaceutical product or pharmaceutical formulation as defined herein for use in the treatment of a gram-negative bacterial infection. Preferably the gram-negative bacterial infection is caused by a bacteria selected from *Enterobacteriaceae, Enterobacter, Pseudomonas* and *Acinetobacter*, e.g. *Enterobacteriaceae or Enterobacter*. In various embodiments, the infection is caused by a (multi) drug-resistant strain of the bacteria.

In a fourth aspect the present invention provides a method of treating a gram-negative bacterial infection comprising the administration of the pharmaceutical product or pharmaceutical formulation as defined herein to a subject in need thereof. Preferably the gram-negative bacterial infection is caused by a bacteria selected from *Enterobacteriaceae, Enterobacter, Pseudomonas* and *Acinetobacter*, e.g. *Enterobacteriaceae or Enterobacter*. In various embodiments, the infection is caused by a (multi) drug-resistant strain of the bacteria.

In a fifth aspect the present invention provides a sealed vial containing the pharmaceutical product or the pharmaceutical formulation as defined herein.

In a sixth aspect the present invention provides a process for preparing a pharmaceutical product in the form of a storage stable lyophilisate, said process comprising: mixing a therapeutically effective amount of a polymyxin selected from polymyxin E, polymyxin B, or a pharmaceutically acceptable derivative thereof, a therapeutically effective amount of zidovudine or a pharmaceutically acceptable derivative thereof and an aqueous carrier to form a solution, sterile filtering the solution, filling one or more vials with the filtered, sterile solution, and subjecting the filled vial(s) to lyophilisation. Each individual vial may have a fill volume per vial of between about 10 ml and about 20 ml. A buffering agent(s) may also be present.

In various embodiments of the present invention, the polymyxin is polymyxin E or a pharmaceutically acceptable derivative thereof. For example, the polymyxin E or pharmaceutically acceptable derivative thereof may be selected from the group consisting of colistin sulfate, colistin methane sulfonate, or colistin methane sulfonate sodium.

In various embodiments of the present invention, the therapeutically effective amount of the polymyxin is between about 0.5 Million International Units (MIU) and about 14 Million International Units (MIU). Preferably the amount of polymyxin is between about 1 MIU and about 12

MIU, more preferably the amount of polymyxin is between about 2 MIU and about 9 MIU; the units used for the dose of the polymyxin are discussed in more detail below.

In various embodiments of the present invention, the therapeutically effective amount of zidovudine is between about 50 mg and about 1500 mg. Preferably the amount of zidovudine is between about 100 mg and about 1000 mg, more preferably between about 150 mg and about 800 mg, and most preferably between about 150 mg and about 500 mg.

In various embodiments of the present invention, the pharmaceutical product or pharmaceutical formulation includes a greater amount of the polymyxin compared to zidovudine, on a w/w basis. For example, the weight ratio of polymyxin to zidovudine may be about 8:1 to about 11:10, such as about 2:1.

In various embodiments of the process of the present invention, the polymyxin is mixed with the aqueous carrier prior to mixing with zidovudine.

These aspects and embodiments are set out in the appended independent and dependent claims. It will be appreciated that features of the dependent claims may be combined with each other and with features of the independent claims in combinations other than those explicitly set out in the claims. Furthermore the approaches described herein are not restricted to specific embodiments such as those set out below, but include and contemplate any appropriate combinations of features presented herein.

BRIEF DESCRIPTION OF THE DRAWINGS

Embodiments of the invention will now be described, by way of example only, with reference to the accompanying drawings, in which:

FIG. 1 is an overlay of CMS peak patterns during the stability study from Example 1A: from the bottom to the top of the graph, the patterns are for the CMS bulk drug substance material, the sample at T0, the sample after 24 hours at 5° C., and after 24 hours at 25° C.

DETAILED DESCRIPTION OF THE INVENTION

Aspects and features of certain examples and embodiments are discussed and described herein. Some aspects and features of certain examples and embodiments may be implemented conventionally and these are not discussed or described in detail in the interests of brevity. It will thus be appreciated that aspects and features of apparatus and methods discussed herein which are not described in detail may be implemented in accordance with any conventional techniques for implementing such aspects and features.

As discussed herein, the invention relates to pharmaceutical products of a polymyxin and zidovudine that exhibit storage stability at both controlled room temperature and accelerated conditions. Surprisingly this pharmaceutical product is a lyophilisate which consists essentially of the two active ingredients and optionally one or more buffering agent(s). In preferred embodiments, the lyophilisate consists of the two active ingredients. In other words, the lyophilisate does not include any excipients that have a material effect on the stability of the lyophilisate or solubility of the actives such as solubilising agents or stabilising agents. This is a surprising solution to the problem of developing a stable pharmaceutical product for the synergistic combination of colistin and zidovudine, because the lyophilisation process is typically reliant on the excipients that are chosen, and lyophilisates almost always include one or more excipients such as polyol stabilising agents in order to stabilise the active agent contained therein. The present inventors were therefore surprised to discover that the combination of a polymyxin and zidovudine does not require any stabilising or solubilizing excipients in order to prepare a storage stable lyophilisate, and that the stable lyophilisate is further suitable for re-constitution with an aqueous carrier (e.g. water) in order to prepare a sterile solution for parenteral administration. This solution may be administered following reconstitution or may be combined with an infusion solution and then administered. The inventors surprisingly found that infusion solutions containing the sterile solution of the invention were stable under both ambient and storage conditions, e.g. at 2-8° C.

The present inventors were also surprised to discover that the carrier for the pharmaceutical formulation consisting of the polymyxin and zidovudine was aqueous. Zidovudine is sparingly soluble in water but the presence of a polymyxin, particularly CMS, was found to enhance the solubility of zidovudine and thereby allow an aqueous solvent system to be employed.

Definitions

As used herein, the expression "consists essentially of" or "consisting essentially of" means that the product or formulation includes the recited, mandatory components, along with other components which do not materially affect the essential characteristics of the composition, e.g. minor amounts of impurities. Notably the expression "consists essentially of" or "consisting essentially of" excludes excipients which have a material effect on the stability of the lyophilisate and/or the solubility of the actives in the aqueous carrier. The present invention is based on the discovery that the polymyxin and zidovudine can be lyophilised into a stable lyophilisate without the need to add any stabilising agents and further formulated in an aqueous solvent system suitable for parenteral administration without the need for any solubilising agents.

With the exception of the optional buffering agent, the term "excipients" is used herein according to the definition of The International Pharmaceutical Excipients Council to refer to "substances other than the pharmacologically active drug or prodrug which are included in the manufacturing process or are contained in a finished pharmaceutical product dosage form". Without being limiting, the term excipients can therefore include bulking agents such as sugars, amino acids and polymers, solubilizing agents such as complexing agents, surfactants and co-solvents, tonicifying agents, additional antimicrobial agents and collapse temperature modifiers.

As used herein, the expression "consists of" or "consisting of" means that the product or formulation only includes the recited, mandatory components.

The term "storage stable" is used herein to mean that the product or formulation is stable when stored under pre-set conditions, e.g. 5° C.±3° C. or room temperature (25° C.), for a pre-determined period of time, e.g. 6 to 30 hours. Stability may be determined by methods known in the art, and can include analysing the formulations after storage for changes in the amount of zidovudine, polymyxin or impurity levels. These changes can be measured using techniques known in the art. For instance, such techniques include high performance liquid chromatography (HPLC), and versions thereof such as reversed phase HPLC (RP-HPLC).

HPLC usually employs pressure to percolate a mobile phase through a column comprising a stationary phase, and the skilled artisan would understand how to perform HPLC and RP-HPLC in order to measure the stability of the formulations. Using HPLC, stability may, for example, be assessed by analysing the generated impurity profile. For example, one measure is the peak area % of the impurities detected by HPLC, or the total peak area % of all impurities detected by HPLC. These measurements may be compared to measurements of the formulation before storage, or may be compared to measurements of a formulation standard.

In various embodiments of the invention, the formulation is storage stable because there are no significant changes in zidovudine, polymyxin and/or impurity levels over the pre-determined period of time. Significance means statistical significance as routinely determined in the art.

Suitable measurement methods for stability are also set out in the Examples. These include a hybrid RP-HPLC method for simultaneously quantifying the purity and quantity of zidovudine and CMS, before and after storage at e.g. 5° C.±3° C. or room temperature (about 25° C.) for 6, 12, 24 or 30 hours. This hybrid method is a modified version of the RP-HPLC method for CMS described in Bai et al., A simple HPLC method for separation of Colistimethate Sodium and Colistin sulphate, *J Chromatograph Separat Techniq* 2011: 2 (1). The method according to Bai et al (which method is incorporated herein by reference) can be carried out to quantify CMS, and then modified to quantify zidovudine. The modifications include reducing the slope of the gradient from 3%/min to 1.5%/min in order to enhance the resolution and separate any impurities from the zidovudine main peak, and increasing the detection wavelength from 214 nm to 265 nm. The chromatographic conditions are set out in Example 1.

Stability of CMS and zidovudine can also be assessed according to the European Pharmacopeia (Ph. Eur.) methods. Such methods are incorporated herein by reference, and include the RP-HPLC method for related substances of CMS-Na according to European Pharmacopeia 9.5 (July 2017:0319); the Determination of free colistin method according to European Pharmacopeia 9.5 (July 2017:0319); and the RP-HPLC method for zidovudine according to monograph Ph.Eur. 9.5 (January 2017:1059).

Other methods suitable for analysing colistimethate sodium or for identifying the various components of CMS include the HPLC method described in WO2014/195405 A1 (Xellia Pharmaceuticals APS), and the HPLC method in water described in Li et al., Antimicro. Agents. Chemo (2003) 47, 4). An analytical method for determining the potency of colistimethate sodium (CMS) in a synergistic antimicrobial combination is disclosed in the co-pending application GB1910777.0. This method is incorporated herein by reference; for the combination of CMS and zidovudine, the potency of CMS in the combination can be determined by using *Pseudomonas Aeruginosa* in an agar diffusion assay.

The term "lyophilisate" is used herein to refer to a material produced by lyophilisation or a freeze-drying process. The specific conditions used for freeze-drying are not limited, and the skilled person would readily be able to determine suitable conditions to obtain a lyophilisate according to the present invention.

The term "sterile" is used herein in the medical context to mean aseptic or free from bacterial or other living microorganisms. The pharmaceutical formulation according to the present invention is a sterile solution in the sense that it can be parenterally administered a subject in need thereof.

The expression "pharmaceutically acceptable derivative thereof" is used herein to refer to a pharmaceutically acceptable prodrug, salt or ester of the particular compound. Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as $(C_1-C_4)$-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as $(C_1-C_4)$-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkane-alcohols of 1-12 carbon atoms which may be unsubstituted or substituted, (e.g. by a halogen).

The present invention also includes solvate forms of the compounds.

The term "therapeutically effective amount" is used herein with reference to amounts useful in a medical context. The particular amount of each active incorporated in the preparation can be determined based on the active and on the intended end-use of the preparation. Therapeutic effective amounts of polymyxin E, polymyxin B and pharmaceutically derivatives thereof are typically expressed in the art with the units "I.U.", "IU", "M.I.U." or "MIU". These acronyms mean "International Units" or "Million International Units". The same nomenclature is used herein.

For polymyxin B and pharmaceutically acceptable derivatives thereof such as polymyxin B sulfate, it is generally accepted in the art that 1 mg is equivalent to approximately 10,000 IU. This means that 5 MIU would equate to 500 mg (10,000×500=5,000,000).

For polymyxin E and pharmaceutically acceptable derivatives thereof such as colistin sulfate, colistin methane sulfonate and colistin methane sulfonate sodium, the meaning of 1 MIU depends on the compound being used and the potency thereof. Colistin base, for instance, has a potency of around 30,000 IU/mg, whereas colistin sulfate has a potency around 20,500 IU/mg, and CMS has a potency of around 12,500 IU/mg. This means that 5 MIU of colistin sulfate with a potency of 20,500 IU/mg, corresponds to an amount of approximately 244 mg, and 5 MIU CMS with a potency of 12,500 IU/mg corresponds to an amount of 400 mg.

The potency of a polymyxin E or derivative thereof is determined according to the European Pharmacopeia microbiological assay of antibiotics: Ph. Eur. 2.7.2. This assay is incorporated herein by reference and is used to determine the activity of the antibiotic by comparing the inhibition of growth of sensitive micro-organisms produced by 3 doses of reference substance, and 3 doses of the antibiotic to be examined. It is well-recognised and understood in the art such that a skilled person would readily be able to convert the IU or MIU units herein to amounts in mg of the antibiotic being used. As noted above, the potency of CMS in the synergistic combination with zidovudine may be determined by the method disclosed in co-pending application GB1910777.0.

It is also known in the art that dosage labels differ between the US and Europe for colistin-based products. In the US, CMS is labelled and dosed according to milligrams of colistin base activity, CBA. CBA is calculated on the basis of International Units and often manufacturers will report both CBA and IU or MIU values. In Europe, CMS is labelled and dosed according to International Units of CMS. The European SmPC for Colomycin includes the following approximate CMS conversion table; this conversion is used herein:

| Potency | | |
|---|---|---|
| IU | ≈ mg CBA | ≈ mass of CMS (mg)* |
| 12 500 | 0.4 | 1 |
| 150 000 | 5 | 12 |
| 1 000 000 | 34 | 80 |
| 4 500 000 | 150 | 360 |
| 9 000 000 | 300 | 720 |

*Nominal potency of the drug substance = 12,500 IU/mg

Combination Product

The pharmaceutical product and pharmaceutical formulation of the present invention are therapeutic combination products for a polymyxin and zidovudine. The polymyxin is selected from polymyxin E, polymyxin B or a pharmaceutically acceptable derivative thereof, and zidovudine is the compound per se or a pharmaceutically acceptable derivative thereof.

Polymyxin E, polymyxin B and zidovudine are well-known in the art and for brevity, are not discussed in detail herein. Polymyxin E is also known as colistin and this compound, along with its pharmaceutically acceptable derivatives such as colistin sulfate, colistin methane sulfonate and colistin methane sulfonate sodium, and polymyxin B or its pharmaceutically acceptable derivatives (e.g. polymyxin B sulfate) may be obtained from a commercial source or by known methods. CMS can, for example, be manufactured by chemical modification of the antibiotic mixture colistin. In particular, the primary amino groups of colistin are converted into methyl sulphonate groups (Barnette et al., Brit. J. Pharmacol. (1964), 23, 552). Commercial sources of the polymyxin active include Sigma-Aldrich, the Livzon Pharmaceutical Group (China) and Xellia Pharmaceuticals ApS (Denmark).

Zidovudine may be obtained by known methods or from commercial sources such as Sigma-Aldrich, Hetero Labs Ltd. (India), or the EDQM (European Directorate for the Quality of Medicines & Healthcare).

Pharmaceutically acceptable derivatives of polymyxin E and polymyxin B are known in the art, and include the well-recognised pro-drugs colistin methane sulfonate, colistin methane sulfonate sodium. Also included are pharmaceutically acceptable salts of polymyxin E and polymyxin B such as colistin sulfate and polymyxin B sulfate.

The pharmaceutical product and formulation of the present invention include the polymyxin and zidovudine at respective therapeutically effective amounts. The term "therapeutically effective amount" is defined above.

In various embodiments, the pharmaceutical product or pharmaceutical formulation are exploited for therapeutic purposes. In particular for use in treatment of a Gram-negative bacterial infection; these infections may be caused by drug-resistant strains of the bacteria, and/or caused by bacteria selected from e.g. *Enterobacteriaceae, Enterobacter, Pseudomonas,* or *Acinetobacter.* This use entails parenteral administration of the reconstituted lyophilisate by injection of a dose that reflects the prescribed treatment regimen.

In various embodiments, the therapeutically effective amount of zidovudine is between about 50 mg and about 1500 mg. Preferably the amount of zidovudine is between about 100 mg and about 1000 mg, more preferably between about 150 mg and about 800 mg, and most preferably between about 150 mg and 500 mg. It will be understood that these weight ranges are combinable with the therapeutically effective amount of the polymyxin discussed below. It will also be understood that these weight ranges are combinable with the other features of the invention discussed herein, for example, the weight ratio of polymyxin to zidovudine.

When administered as an injection volume of e.g. about 20 ml, the above amounts of zidovudine correspond to concentration ranges of between about 2.5 mg/ml and about 75 mg/ml, preferably between about 5 mg/ml and about 50 mg/ml, more preferably between about 7.5 mg/ml and about 40 mg/ml and most preferably between about 7.5 mg/ml and about 25 mg/ml. Other injection volumes are of course possible, and the skilled person is readily able to convert the required therapeutically effective amount of zidovudine in mg into a concentration of mg/ml.

As explained above, amounts of polymyxin antibiotics are conventionally reported in International Units or Million International Units. In various embodiments the therapeutically effective amount of the polymyxin or the pharmaceutically acceptable derivative thereof is between about 5000 IU and about 14 MIU. Preferably between about 5000 IU and about 12 MIU, and more preferably between about 5000 IU and about 9 MIU.

When the polymyxin is polymyxin B or a pharmaceutically acceptable derivative thereof (e.g. polymyxin B sulfate), the therapeutically effective amount of the polymyxin in the pharmaceutical product or pharmaceutical formulation of the present invention is between about 5000 IU and about 5 MIU. Preferably between about 5000 IU and about 4 MIU and more preferably between about 5000 IU and about 1 MIU.

When the polymyxin is polymyxin E or a pharmaceutically acceptable derivative thereof (e.g. colistin sulfate, colistin methane sulfonate or colistin methane sulfonate sodium), the therapeutically effective amount of the polymyxin in the pharmaceutical product or pharmaceutical formulation of the present invention is between about 0.5 MIU and about 14 MIU. Preferably between about 1 MIU and about 12 MIU, more preferably between about 2 MIU and about 9 MIU, and most preferably between about 2 MIU and about 5 MIU.

When the polymyxin is CMS with a potency of 12,500 IU/mg, these values correspond to amounts of between about 40 mg and about 1,120 mg, preferably between about 80 mg and about 960 mg, more preferably between about 160 mg and about 720 mg, and most preferably between about 160 mg and about 400 mg.

In various embodiments of the present invention, the pharmaceutical product or formulation contains polymyxin B or a pharmaceutically acceptable derivative thereof in an amount of between about 5000 IU and about 5 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin B or a pharmaceutically acceptable derivative thereof in an amount of between about 5000 IU and about 4 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin B or a pharmaceutically acceptable derivative thereof in an amount of between about 5000 IU and about 1 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin E or a pharmaceutically acceptable derivative thereof in an amount of between about 0.5 MIU and about 14 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin E or a pharmaceutically acceptable derivative thereof in an amount of between about 1 MIU and about 12 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin E or a pharmaceutically acceptable derivative thereof in an amount of between about 2 MIU and about 9 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

In various embodiments of the present invention, the pharmaceutical product or formulation contains polymyxin E or a pharmaceutically acceptable derivative thereof in an amount of between about 2 MIU and about 5 MIU, and zidovudine or a pharmaceutically acceptable derivative thereof in an amount of between about 50 mg and about 1500 mg. Preferably zidovudine is present in an amount of between about 100 and about 1000 mg, more preferably between about 150 mg and about 800 mg, most preferably between about 150 mg and about 500 mg.

It can be seen from the Examples of this application how preferred embodiments include the polymyxin in an amount greater than the amount of zidovudine, on a w/w basis. In particular, when the amount of polymyxin in IU or MIU is converted to a weight of X mg and zidovudine is included at a weight of Y mg, X>Y. In more preferred embodiments, a weight ratio of polymyxin to zidovudine can be defined. Suitable weight ratios of polymyxin to zidovudine are disclosed in WO 2017/098274 A1, these weight ratios are incorporated herein by reference. More preferred weight ratios are, however, between about 8:1 to about 11:10 (polymyxin:zidovudine).

In various embodiments of the invention, the weight ratio of polymyxin to zidovudine is therefore between about 8:1 to about 11:10. Preferably between about 6:1 to about 9:7, more preferably between about 5:1 to about 6:4, and most preferably between about 3:1 to about 2:1.

As noted above, in preferred embodiments the pharmaceutical product and pharmaceutical formulation of the present invention do not include any excipients other than the optional buffering agent(s). The term "consisting essentially of" is used herein to define the pharmaceutical product and pharmaceutical formulation in such a way that other non-defined excipients are excluded. Such excipients are well-known in the art, and include those which have regulatory acceptance as they are intended for parenteral administration. Examples are bulking agents, solubilizing agents, tonicifying agents or modifiers, additional antimicrobial agents and collapse temperature modifiers.

Bulking agents, as the name implies, form the bulk of the lyophilised product and provide an adequate structure to the cake. They are also referred to herein as stabilising agents, and can be sugars, such as mannitol, lactose, sucrose, trehalose, sorbitol, glucose and raffinose, amino acids such as arginine, glycine and histidine, or polymers such as dextran and polyethylene glycol. Mannitol and glycine are the most commonly used bulking agents, followed by glucose, sucrose, lactose, trehalose and dextran.

Solubilizing agents are added where the drug solubility is low or when the drug is crystalline and either remains amorphous after lyophilisation or is difficult to crystallise. They can be complexing agents such as EDTA and cyclodextrins, surfactants such as the polysorbates (e.g. polysorbate 80), or co-solvents such as tert-butyl alcohol, iso-propyl alcohol, dichloromethane, ethanol, acetone and glycerol. Surfactants are typically added to low dose products to minimize losses due to surface adsorption. Co-solvents may be used to increase the primary drying rate by increasing the sublimation rates, improve product stability, decrease reconstitution time by improving drug wettability or solubility, and also enhance the sterility assurance of the sample solution.

Tonicifying agents or modifiers are added to ensure that parenteral formulations are isotonic with human plasma. Examples include sodium chloride, sucrose, mannitol and dextrose, although dextrose is the most commonly used. Additional antimicrobial agents can be added when a product is intended for multiple uses and/or to prevent microbial growth during its shelf life. Examples include benzyl alcohol, phenol, m-cresol, methyl paraben, ethyl paraben and mixtures thereof.

Lyophilisation of amorphous material requires the primary drying temperature to be kept below the collapse temperature of the formulation. However, some excipients in an amorphous state have a very low collapse temperature, thus increasing the duration of primary drying significantly. In such cases, collapse temperature modifiers are used to shift the overall collapse temperature higher, thereby reducing the primary drying cycle without compromising the product quality. Examples include dextran, hydroxyethyl starch, Ficoll® and gelatin.

The optional one or more buffering agent may be included when a particular pH is desired, and may be any acid or salt combination which is pharmaceutically acceptable and capable of maintaining the solution at a certain pH range, e.g. acetate, tartrate or citrate sources. The buffering agent may be selected from the group consisting of citric acid, sodium citrate, potassium citrate, tartaric acid, sodium phosphate, sodium acetate, potassium acetate and mixtures thereof.

In various embodiments, the pharmaceutical product or pharmaceutical formulation does not include a bulking agent. In various embodiments the pharmaceutical product or pharmaceutical formulation does not include a bulking agent selected from sugars, amino acids and polymers.

The pharmaceutical formulation of the present invention is suitable for parenteral administration. As used herein, parenteral administration refers to injection directly into the body, bypassing the skin and mucous membranes. In various embodiments, parenteral administration refers to intradermal, intraperitoneal, intramuscular, subcutaneous and intravenous administration. Preferably the pharmaceutical formulation of the present invention is suitable for intravenous administration. Accordingly the pharmaceutical formulation is in the form of a solution, notably a sterile solution, due to the presence of an aqueous carrier.

In various embodiments, the pharmaceutical formulation of the present invention is a single-vial injection concentrate which is a sterile liquid in a single vial ready to dilute with an infusion solution. In other embodiments, the pharmaceutical formulation is a dual-vial injection concentrate which requires mixing with a diluent before it can be further diluted with an infusion solution, or a diluted injection concentrate which is a dual-vial injection concentrate mixed with the diluent, ready for further dilution with an infusion solution. Alternatively the pharmaceutical formulation is a final dilution for infusion which is a single-vial injection concentrate or diluted injection concentrate, combined with an infusion solution and ready to be administered.

The aqueous carrier included in the pharmaceutical formulation of the present invention may therefore refer to the liquid used to prepare the single-vial injection concentrate, the diluent and/or the infusion solution. An infusion solution is typically a sterile isotonic solution that is employed to dilute an injection concentrate for administration to a patient. On this basis, the aqueous carrier may be defined as a pharmaceutically acceptable liquid which contains water as the main solvent. In various embodiments the aqueous carrier is at least about 75 wt % water. In various embodiments the aqueous carrier is at least about 80 wt % water, preferably at least about 85 wt %, more preferably at least about 90 wt % and most preferably at least about 95 wt % water.

In various embodiments the aqueous carrier may further be selected from the group consisting of water, saline solution and sugar solution, e.g. a glucose or dextrose solution. For example, the aqueous carrier may be a 0.9 wt % saline (sodium chloride) solution, a 5 wt % glucose solution or a 5 wt % dextrose solution. The present invention is not, however, limited to these specific examples and other pharmaceutically acceptable aqueous carriers are known in the art and may be used herein.

In various embodiments the aqueous carrier does not include any organic solvent(s).

Medical Use

The present invention further provides the pharmaceutical product and pharmaceutical formulation as defined herein for use in the treatment of a Gram-negative bacterial infection. Also provided by the present invention is a method of treating a Gram-negative bacterial infection comprising the administration of the pharmaceutical product or pharmaceutical formulation as defined herein to a subject in need thereof.

In particular the pharmaceutical product or pharmaceutical formulation may be used to kill multiplying and/or clinically latent bacteria associated with the Gram-negative bacterial infections. References herein to the treatment of a bacterial infection therefore include killing multiplying and/or clinically latent bacteria associated with such infections. Preferably, the product and formulation of the present invention are used to kill clinically latent bacteria associated with Gram-negative bacterial infections.

As used herein, "kill" means a loss of viability as assessed by a lack of metabolic activity.

As used herein, "clinically latent bacteria" means bacteria that is metabolically active but has a growth rate that is below the threshold of infectious disease expression. The threshold of infectious disease expression refers to the growth rate threshold below which symptoms of infectious disease in a host are absent. The metabolic activity of clinically latent bacteria can be determined by several methods known to those skilled in the art; for example, by measuring mRNA levels in the bacteria or by determining their rate of uridine uptake. In this respect, clinically latent bacteria, when compared to bacteria under logarithmic growth conditions (in vitro or in vivo), possess reduced but still significant levels of:

(i) mRNA (e.g. from 0.0001 to 50%, such as from 1 to 30, 5 to 25 or 10 to 20%, of the level of mRNA); and/or (ii) uridine (e.g. [³H]uridine) uptake (e.g. from 0.0005 to 50%, such as from 1 to 40, 15 to 35 or 20 to 30% of the level of [³H]uridine uptake).

Clinically latent bacteria typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent bacteria are phenotypically tolerant, and as such are sensitive (in log phase) to the biostatic effects of conventional antimicrobial agents (i.e. bacteria for which the minimum inhibitory concentration (MIC) of a conventional antimicrobial is substantially unchanged); but possess drastically decreased susceptibility to drug-induced killing (e.g. bacteria for which, with any given conventional antimicrobial agent, the ratio of minimum microbicidal concentration (e.g. minimum bactericidal concentration, MBC) to MIC is 10 or more).

As used herein, the term "bacteria" (and derivatives thereof, such as "bacterial infection") includes, but is not limited to, references to organisms (or infections due to organisms) of the following classes and specific types:

Gram-negative cocci, such as:

*Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri; Enterobacteriaceae,* such as *Escherichia coli, Enterobacter* (e.g. *Enterobacter aerogenes, Enterobacter agglomerans* and *Enterobacter cloacae*), *Citrobacter* (such as *Citrobacter freundii* and *Citrobacter divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebsiella pneumoniae, Klebsiella oxytoca, Klebsiella omitholytica, Klebsiella planticola, Klebsiella ozaenae, Klebsiella terrigena, Klebsiella granulomatis* (*Calymmatobacterium granulomatis*) and *Klebsiella rhinoscleromatis*), *Proteus* (e.g. *Proteus mirabilis, Proteus rettgeri* and *Proteus vulgaris*), *Providencia* (e.g. *Providencia alcalifaciens, Providencia rettgeri* and *Providencia stuartii*), *Serratia* (e.g. *Serratia marcescens* and *Serratia liquifaciens*), *Yersinia* (e.g. *Yersinia enterocolitica, Yersinia pestis* and *Yersinia pseudotuberculosis*); *Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. lwoffi* and *A. radioresistens*); *Pseudomonas* (e.g. *Pseudomonas aeruginosa, Pseudomonas maltophilia* (*Stenotrophomonas maltophilia*), *Pseudomonas alcaligenes, Pseudomonas chlororaphis, Pseudomonas fluorescens, Pseudomonas luteola. Pseudomonas mendocina, Pseudomonas monteilii, Pseudomonas oryzihabitans, Pseudomonas pertocinogena, Pseudomonas pseudalcaligenes, Pseudomonas putida* and *Pseudomonas stutzen*); *Bacteroides fragilis; Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*); *Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*); *Brucella* (e.g. *Brucella abortus, Brucella canis, Brucella melintensis* and *Brucella suis*); *Campylobacter* (e.g. *Campylobacter jejuni, Campylobacter coli, Campylobacter lari* and *Campylobacter fetus*); *Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*); Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); *Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*); *Rickettsia* (e.g. Rickettsii or *Coxiella burnetii*); *Legionella* (e.g. *Legionella anisa, Legionella birminghamensis, Legionella bozemanii, Legionella cincinnatiensis, Legionella dumoffii, Legionella feeleii, Legionella gormanii, Legionella hackeliae, Legion-*

*ella israelensis, Legionella jordanis, Legionella lansingensis, Legionella longbeachae, Legionella maceachernii, Legionella micdadei, Legionella oakridgensis, Legionella pneumophila, Legionella sainthelensi, Legionella tucsonensis* and *Legionella wadsworthii*); *Moraxella catarrhalis;* *Stenotrophomonas maltophilia; Burkholderia cepacia; Burkholderia mallei* and *Burkholderia pseudomallei; Francisella tularensis; Gardnerella* (e.g. *Gardneralla vaginalis* and *Gardneralla mobiluncus*); *Streptobacillus moniliformis*; Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*); *Bartonella* (*Bartonella bacilliformis, Bartonella clarridgeiae, Bartonella elizabethae, Bartonella henselae, Bartonella quintana* and *Bartonella vinsonii arupensis*); *Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*); *Spirillium* (e.g. *Spirillum minus*); *Bacteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*); *Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*); *Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*); *Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*); *Chlamydia* (e.g. *Chlamydia trachomatis*); *Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*)); *Leuconostoc* (e.g. *Leuconostoc* citreum, *Leuconostoc cremoris, Leuconostoc dextranicum, Leuconostoc lactis, Leuconostoc mesenteroides* and *Leuconostoc pseudomesenteroides*); and *Gemella* (e.g. *Gemella bergeri, Gemella haemolysans, Gemella morbillorum* and *Gemella sanguinis*).

Particular bacteria that may be treated using a product or formulation of the invention include: *Enterobacteriaceae*, such as *Escherichia coli, Klebsiella* (e.g. *Klebsiella pneumoniae* and *Klebsiella oxytoca*) and *Proteus* (e.g. *Proteus mirabilis, Proteus rettgeri* and *Proteus vulgaris*); *Enterobacter, Pseudomonas* and *Acinetobacter*. Preferably, the bacterium is *Enterobacteriaceae*, such as *Escherichia coli, Klebsiella* (e.g. *Klebsiella pneumoniae* and *Klebsiella oxytoca*) and *Proteus* (e.g. *Proteus mirabilis, Proteus rettgeri* and *Proteus vulgaris*) or *Enterobacter*. Most preferably, the bacterial infection treated is an infection caused by one or more of *E. coli, Klebsiella pneumoniae* or *Enterobacter*. In all embodiments the combination therapy is synergistic as compared to the administration of the combination components taken alone. The pharmaceutical product and pharmaceutical formulation of the present invention are particularly beneficial in treating (multi)-drug-resistant ((M)DR) bacteria. With respect to *Enterobacteriaceae*, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebsiella Pneumoniae*. It should be kept in mind that although a combination such as that claimed may initially be demonstrated to be functional in treating (M)DR strains; they can then be used in treating non-resistant strains. This is especially valuable in the context of the presently claimed combination where the primary therapy for *Enterobacteriaceae* is anti-microbial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

Particular conditions which may be treated using the pharmaceutical product or pharmaceutical formulation of the present invention include abscesses, bone and joint infections, burn wounds, cystitis, empyema, endocarditis, enteric fever, epididymitis, eye infections, furuncles, genital infections, granuloma inguinale, infected burns, infections following dental operations, infections associated with prostheses, intraabdominal abscesses, liver abscesses, mastoiditis, infections of the nervous system, osteomyelitis, orchitis, pancreatitis, pelveoperitonitis, peritonitis, peritonitis with appendicitis, pleural effusion, postoperative wound infections, prostatitis, pyelonephritis, pyoderma (e.g. impetigo), salmonellosis, salpingitis, septic arthritis, typhoid, and wound infections; or infections with *Escherichia coli, Klebsiella pneumoniae, Klebsiella oxytoca, Proteus mirabilis, Proteus rettgeri,* and *Proteus vulgaris.*

It will be appreciated that references herein to "treatment" extend to prophylaxis as well as the treatment of established diseases or symptoms.

The pharmaceutical product or pharmaceutical formulation of the invention may be presented in unit dosage form, and may be prepared by any of the methods well known in the art of pharmacy e.g. as described in "*Remington: The Science and Practice of Pharmacy*", Lippincott Williams and Wilkins, 21$^{st}$ Edition, (2005). In preferred embodiments the pharmaceutical product is prepared according to the process of the invention described herein.

Preparation Process

In various embodiments of the invention, the pharmaceutical product of the invention is prepared according to the process of the invention. In this process, a therapeutically effective amount of a polymyxin as defined above, a therapeutically effective amount of zidovudine as defined above, and an aqueous carrier as defined above, is mixed to form a solution. This solution is sterile-filtered, transferred to one or more vials, and the filled vial(s) then lyophilised. The fill volume of each individual vial may be between about 10 ml and about 20 ml.

The addition of the components (i.e. the polymyxin, zidovudine and aqueous carrier) can be achieved by methods known in the art. For example, one or more of the components may be added to each other and then into a common receptacle for mixing, or the components may be added to a common receptacle in a particular order, or the components may be added to a common receptacle simultaneously. In various embodiments the aqueous carrier may be added to a receptacle, followed by the addition of the polymyxin and the zidovudine. In various embodiments the polymyxin and zidovudine and added simultaneously. In other embodiments the polymyxin is added first, followed by the zidovudine.

The components may further be mixed by methods known in the art. For example, the components can be mixed by simple mixing, or may be mixed with a mixing device continuously, periodically, or a combination thereof. Mixing devices may include, but are not limited to, a magnetic stirrer, shaker, a paddle mixer, homogenizer, and any combination thereof. The addition and mixing of one or more components may occur under controlled conditions. For example, the addition and mixing of the components may occur under conditions such as under nitrogen or at a particular humidity, etc., or the adding and mixing may occur under certain temperatures. In certain embodiments, the adding and mixing may occur under temperature conditions of about 5° C. to about 40° C. Additionally, the addition and mixing may be under controlled light exposure, such as in yellow light or under protection from direct exposure to light.

After the solution is prepared, it is sterilized by sterile or aseptic filtration. For example, the solution can be filtered using a 0.2 μm disposable pre-sterilized membrane filter or other suitable filters known in the art. The sterile solution is then filled into one or more pre-sterilized vials and stoppered aseptically, before undergoing lyophilisation.

Lyophilisation is a freeze-drying process which is well-characterised in the art. It is a process in which water is frozen, and removed from the sample in typically, two stages. The first, labelled "primary drying" involves sublimation, and the second, labelled "secondary drying" is by desorption. In the majority of lyophilised formulations, excipients are included to improve the functional properties and stability of the lyophilised product. The present invention does not, however, involve the use of such excipients. The lyophilisation process carried out as part of the process of the present invention is not limited and would be readily determined by the skilled person. Once lyophilised, the vials may be stored under temperatures of about 2 to about 10° C.

The present disclosure will now be exemplified with reference to the following non-limiting examples.

EXAMPLES

Example 1: Solubility Testing

The objective of Example 1 was to provide a mixed drug product containing CMS or colistin methane sulfonate sodium and zidovudine. CMS is an inactive prodrug which is enzymatically hydrolysed into colistin sulfate, a salt of the antimicrobial agent polymyxin E, after parenteral application. The anti-retroviral agent zidovudine is also a prodrug that needs to be tri-phosphorylated to become effective and acts as an antibiotic resistance breaker (ARB). Colistin sulfate and zidovudine are two registered medications which need to be combined into one antibiotic combination drug product. This has, however, never been done before and as a potential solubility discrepancy between the 2 actives cannot be excluded, the inventors carried out detailed solubility and stability tests to identify a common, compatible solvent.

A) Solubility and Stability in an Aqueous Solvent System

In order to identify a common, compatible solvent for both actives, a screening of CMS, zidovudine and the combination was performed in an aqueous solvent system. A two component buffer system consisting of acetate and phosphate (5 mM acetate and 5 mM phosphate) was used to cover a pH range of about 4.5 to 7.5. After complete dissolution of the solid, the pH was adjusted to the desired pH value using hydrochloric acid.

The target dose was set to 400 mg CMS and 200 mg zidovudine per vial, and substances were dissolved in an appropriate solvent volume suitable for lyophilisation: 10 ml to 20 ml. Target concentration was 40 mg/mL CMS (400 mg in 10 mL) and 20 mg/mL zidovudine (200 mg in 10 mL). If the solid did not dissolute at the target concentration, additional buffer was added to achieve a concentration of 20 mg/mL CMS and 10 mg/mL zidovudine.

Samples were tested for stability of the actives in solution when stored for 24 hours at 2-8° C. and 25° C. as shown in Table 1. Samples were analysed prior and after storage with a hybrid RP-HPLC method as described below.

TABLE 1

| Stability storage conditions in buffered aqueous systems | | |
| --- | --- | --- |
| per variant (#1-#12) | T0 | T24 h |
| 2-8° C. | 2 vials | 2 vials |
| 25° C. | | 2 vials |

Materials and Methods

Table 2 lists the materials used in Example 1A. All were obtained from commercial sources.

TABLE 2

| Materials |
| --- |
| Zidovudine |
| Colistimethate sodium (CMS) |
| Acetonitrile, Chromosolv gradient |
| Trifluoroacetic acid, ≥99.9% |
| Acetic acid, 100% |
| Hydrochloric acid 25% |
| Sodium hydroxide pellets, |
| ortho-phosphoric acid 85% |
| Demineralized water <0.2 μS/cm |

A hybrid RP-HPLC method was used in order to simultaneously quantify the purity and quantity of zidovudine and CMS. This hybrid method was a modified version of the RP-HPLC method for CMS described in Bai et al., (A simple HPLC method for separation of Colistimethate Sodium and Colistin sulphate, *J Chromatograph Separat Techniq* 2011: 2 (1)). The method was carried out according to Bai et al (which method is incorporated herein by reference) to quantify CMS and then modified to quantify zidovudine. The modifications were reducing the slope of the gradient from 3%/min to 1.5%/min in order to enhance the resolution and separate any impurities from the zidovudine main peak, and increasing the detection wavelength from 214 nm to 265 nm. The following chromatographic conditions were used:

Column: Discovery HS C18, 4.6×150 mm, 5 μm

Mobile phase A: 0.05% TFA in purified water

Mobile phase B: 0.05% TFA in acetonitrile

| | Time [min] | % B |
|---|---|---|
| Flow gradient: | 0.0 | 15 |
| | 2.0 | 15 |
| | 25.0 | 50 |
| | 25.1 | 100 |
| | 30.1 | 100 |
| | 30.2 | 15 |
| | 35.0 | 15 |

| | |
|---|---|
| Flow rate | 1.0 mL/min |
| Column temperature | 25° C. |
| Injected amount | 5-20 µL |
| Auto-sampler temperature | 5° C. |
| UV detection | 214 nm or 265 nm |

Mobile phase A was prepared by adding 0.5 mL TFA to 1000 mL purified water. Mobile phase B was prepared by adding 0.5 mL TFA to 1000 mL ACN. Samples and bulk drug substance were dissolved at 2 mg/mL in mobile phase A for CMS and at 1 mg/mL for zidovudine.

Results and Conclusions

Both actives were soluble in the aqueous solvent system at all pH values. CMS was also found to show a strong buffer capacity at neutral to slightly basic pH values as all solutions with CMS showed a pH between 7.1 and 7.8. Zidovudine did not affect the pH value of the solution.

No degradation products of zidovudine were observed during the stability screening. Zidovudine seems to be stable in aqueous solution independent of the pH (between 4.5 and 7.5). CMS was most stable at pH 7.5 as the peak pattern was found to correspond to the CMS bulk material after 24 hours at 25° C. (see FIG. 1).

An aqueous solvent system with a fill volume of 20 ml is therefore a promising candidate for the pharmaceutical formulation of CMS and zidovudine.

B) Solubility and Stability in an Organic Solvent System

Following the results of Example 1A, further screening was conducted with an organic solvent system. A screening of C, Z, and C+Z was performed by varying the concentration of organic solvent tert-butanol (TBA). The target dose was set to 240 mg CMS and 200 mg zidovudine per vial. Substances were dissolved in an appropriate volume to justify the use of an organic solvent based system (reduction of the fill volume per vial by a factor of 4, ~5 mL fill volume in organic solvent based systems). Samples were tested for stability of the APIs in solution when stored for 24 h at 2 to 8° C. and 25° C. (see 9861Error! Reference source not found. above), and samples were analysed prior to and after storage by the hybrid RP-HPLC method described above. The chromatographic conditions were the same as set out above for Example 1A.

Materials

The following materials were used (Table 3). all were obtained from commercial sources:

TABLE 3

| Materials |
|---|
| Zidovudine* |
| Colistimethate sodium (CMS)* |
| Promixin |
| Acetonitrile, Chromosolv gradient grade |

TABLE 3-continued

| Materials |
|---|
| Trifluoroacetic acid, ≥99.9% |
| tert-Butanol |
| Demineralized water |
| <0.2 µS/cm |

*used as API (BDS material) for subsequent DP development

Results and Conclusions

In the solubility tests, the TBA concentration was varied between 20% (w/w) and 60% (w/w) in four steps. Target concentration was 48 mg/mL CMS (240 mg in 5 mL) and 40 mg/mL zidovudine (200 mg in 5 mL).

CMS was found to be soluble in all TBA concentrations at 5 mL. The solid dissolved within a few minutes. Zidovudine was not soluble in 5 mL of a 20% TBA solution (the solid was allowed to dissolve for 30 min under agitation), but was soluble in 5 mL of 30%, 50% and 60% TBA. For the mixture of CMS and zidovudine, the same results as for zidovudine alone were observed (complete dissolution of all solid in 5 mL 30%, 50% and 60% TBA).

In the stability studies, the C+Z solutions with a TBA content of 30%, 50% and 60% TBA were monitored after preparation and after storage for 24 hours at ambient temperature and 5° C., respectively. No degradation products of zidovudine were observed at either 25° C. or 5° C. during the stability screening of the mixed C+Z solution. At 30% TBA some precipitation at 5° C. was visually observed in the vial. However, peak area of zidovudine and also CMS remained unchanged in the hybrid RP-HPLC. Most likely zidovudine was precipitated due to lower solubility in 30% TBA in the cold. The amount of precipitated zidovudine was too low to be quantified by RP-HPLC.

Unfortunately the peak pattern from CMS in mixed C+Z DP dissolved in TBA based solvent systems showed differences to the CMS reference dissolved in water. The reason for the different peak pattern of CMS dissolved in TBA based solvent systems was believed to be grounded in the formation of different methane sulfonic acid derivatives formed/present in TBA than in water, but this was not clear and could not be verified by further peak evaluation.

Example 2: Lyophilisation with the Organic Solvent System

To determine whether the organic solvent system was suitable for producing the lyophilisate of C+Z, lyophilisation testing was performed on the combination of C+Z dissolved in TBA/water mixtures. The formulations described in Table 4 were lyophilised:

TABLE 4

| | Variant 1 - 50% TBA | | Variant 2 - 60% TBA | |
|---|---|---|---|---|
| Description | Amount per vial | Description | Amount | |
| CMS | 0.24 g | CMS | 0.24 g |
| Zidovudine | 0.20 g | Zidovudine | 0.20 g |
| 50% TBA | 4.56 g | 60% TBA | 4.56 g |
| Total weight | 5.00 g | Total weight | 5.00 g |
| Fill volume | 5.38 mL | Fill volume | 5.68 mL |

The formulations were compounded and filled into cleaned and heat-sterilized 20R glass vials. Filled vials were then stoppered with autoclaved and dried lyo stoppers, sealed in lyo-bags and loaded into a freeze dryer. Samples were freeze dried using a suitable lyo-cycle. For each variant 10 vials were prepared. The chamber pressure was monitored and recorded via on-line data acquisition to detect the end of sublimation. Samples were then analyzed immediately after lyophilisation (T0) by degradation profile.

Materials

Table 5 lists the materials used in Example 2. All were obtained from commercial sources.

TABLE 5

| Materials |
| --- |
| Zidovudine BDS |
| Colistimethate sodium (CMS) BDS |
| Tungstosilicic acid hydrate |
| Hexamethylentetramine |
| Hydrazine sulfate |
| Demineralized water |
| tert-Butanol |

Methods

Determination of Free Colistin:

Determination of free colistin was performed according to European Pharmacopeia 9.5 (July 2017:0319).

Preparation of Hydrazine Sulfate Solution:

1.0 g of hydrazine sulfate was dissolved in purified water, diluted to 100.0 mL with the same solvent and allowed to stand for 4-6 h.

Preparation of Hexamethylene Tetramine Solution:

2.5 g of hexamethylene tetramine was dissolved in 25.0 mL purified water in a 100 mL glass-stoppered volumetric flask.

Preparation of the Primary Opalescent Suspension:

25.0 mL hydrazine sulfate solution was added to the hexamethylene tetramine solution in the volumetric flask, mixed and allowed to stand for 24 h.

Preparation of the Standard for Opalescence:

15.0 mL of the primary opalescent suspension was diluted to 1000.0 mL with purified water. This suspension was freshly prepared and stored for a maximum of 24 h.

Preparation of Reference Suspensions:

Reference suspensions according to Table 6 were prepared for calibration of the turbidity meter.

TABLE 6

|  | I | II | III | IV |
| --- | --- | --- | --- | --- |
| Standard of opalescence | 5.00 mL | 10.0 mL | 30.0 mL | 50.0 mL |
| Purified water | 95.0 mL | 90.0 mL | 70.0 mL | 50.0 mL |

Assay for Free Colistin According to European Pharmacopeia 9.5:

One lyophilisate containing 240 mg CMS was dissolved in 10 mL purified water. CMS BDS was analyzed by dissolving 80 mg of CMS BDS in 3 mL purified water. After complete dissolution, 0.1 mL 100 g/mL silicotungstic acid was added to 3 mL of the test sample (either reconstituted lyophilisate or dissolved BDS). The turbidity of the sample was recorded after 10 s-20 s. The solution must not be significantly more turbid than standard of opalescence II.

Freeze Drying Procedure:

Vials were washed with purified water. Afterwards the vials were dried and heat-treated. Stoppers were autoclaved and subsequently dried. The formulated bulk solutions were compounded according to Table 104 above. CMS and zidovudine were weighed in a beaker. TBA/water mixtures were added. The solution was stirred at ambient temperature until complete dissolution was observed. Vials were filled with 5 g formulated bulk solution by pipetting. Stoppers were manually placed in lyophilisation position. Product vials were placed on stainless steel racks, sealed in lyo bags and loaded into the freeze dryer. Pressure control was performed via a pressure gauge using the dosing and the vacuum valve. The freeze-drying cycle set out in Table 7 was performed.

TABLE 7

| Step | | Shelf temperature | Ice condenser temperature | Pressure | Time step |
| --- | --- | --- | --- | --- | --- |
| # | Description | [° C.] | [° C.] | [mbar] | [h:min] |
| 1 | Loading | 25 | — | 1000 | 00:01 |
| 2 | Freezing | −45 | — | 1000 | 01:00 |
| 3 | Freezing | −45 | — | 1000 | 05:00 |
| 4 | Vacuum adjustment | −45 | −70 | 0.05 | 00:30 |
| 5 | Primary drying | −10 | −70 | 0.05 | 01:30 |
| 6 | Primary drying | −10 | −70 | 0.05 | 45:00 |
| 7 | Secondary drying | 30 | −70 | 0.05 | 08:00 |
| 8 | Secondary drying | 30 | −70 | 0.05 | 08:00 |

After completion of the lyophilisation cycle the freeze-drying chamber was vented to 750 mbar with nitrogen and vials were closed by collapsing the lyo-shelves towards each other. After venting to atmospheric pressure vials were unloaded, capped and stored at 5° C.

Results

The lyophilisates of the test lyophilisation in organic solvent systems were analyzed for free colistin. Table 8 gives an overview of the obtained results.

TABLE 8

| Sample | Turbidity [NTU] | Acceptance criteria/ not more turbid than standard of opalescence II |
| --- | --- | --- |
| standard of opalescence II | 7.4 | — |
| CMS BDS | 5.5 | yes |
| 50% TBA lyophilisate sample 1 | 39.8 | no |
| 50% TBA lyophilisate sample 2 | 41.8 | no |
| 60% TBA lyophilisate sample 1 | 73.9 | no |
| 60% TBA lyophilisate sample 2 | 37.4 | no |

Both lyophilisates (50% TBA and 60% TBA) contain significant amounts of free colistin, meaning that neither is a stable product which can be used commercially.

Conclusion

The level of free colistin in the organic solvent-based lyophilisates was not acceptable. As such, the TBA solvent system is not suitable for the combination drug product.

It is known in the art that CMS is stable against hydrolysis due to the formation of micelles in aqueous solutions above 3.5 mM (~5.7 mg/mL) (Wallace S J, Li J, Nation R L, Prankerd R J, Velkov T, Boyd B J. Self-Assembly behavior of Colistin and its prodrug Colistin Methansulfonate: Implications for solution stability and solubilization, *J Phy. Chem B,* 2010; 114, p. 4836-4840). Below this concentration rapid hydrolysis of CMS to colistin has been observed (Wallace S J, Li J, Rayner C R, Coulthard K, Nation R L. Stability of Colistin Methanesulfonate in Pharmaceutical Products and Solutions for Administration to Patients. *Antimicrob. Agents Chemother,* 2008, p. 3047-3051).

Without wishing to be bound by any one theory, the inventors believed that the organic solvent TBA, which is contained in the lyo solution, may switch the critical micelle concentration (CMC) of CMS towards a higher concentration resulting in instability of CMS in organic lyo solutions against hydrolysis at the used concentration of 48 mg/mL. Based on the data obtained for 50% TBA/water and 60% TBA/water mixture, lyophilisation of CMS containing drugs using organic solvent based lyo solutions is not possible.

Example 3: Lyophilisation with Aqueous Solvent System

Example 3 looked at the possibility of a freeze-dried presentation of the mixed drug product with aqueous based solvent systems. Formulations were compounded and filled into cleaned and heat-sterilized 30R glass vials. Filled vials were stoppered with autoclaved and dried lyo stoppers, sealed in lyo-bags and loaded into a freeze dryer. Samples were freeze dried using the same lyo-cycle as Example 2. For each variant, 10 vials were prepared. The chamber pressure was monitored and recorded via on-line data acquisition to detect the end of sublimation. Samples were analyzed immediately after lyophilisation (T0) for reconstitution speed and behavior; degradation profile with Ph. Eur. methods for CMS and zidovudine; and residual water content using a generic Karl-Fischer oven method.

Materials

Table 9 lists the materials used in Example 3. All materials were from a commercial source.

TABLE 9

| Materials |
| --- |
| Zidovudine BDS |
| Zidovudine reference standard, for SST, |
| impurity B and impurity D |
| Colistimethate sodium (CMS) BDS |
| Colistimethate sodium (CMS) reference standard |
| E1 colistimethate sodium for peak identification |
| E2 colistimethate sodium for peak identification |
| Acetonitrile, Chromosolv gradient grade |
| Trifluoroacetic acid |
| Sodium dihydrogen phosphate dihydrate |
| Sodium hydroxide pellets |
| Methanol |
| Tungstosilicic acid hydrate |
| Hexamethylentetramine |
| Hydrazine sulfate |
| Ammonium acetate A |
| Demineralized water |

Methods

RP-HPLC for Related Substances of CMS-Na:

The RP-HPLC method for related substances of CMS-Na was performed according to European Pharmacopeia 9.5 (July 2017:0319). The following chromatographic conditions were used:

Column Acquity CSH C18, 2.1×150 mm, 1.7 µm

Acquity CSH C18 VanGuard Pre-Column, 2.1×5 mm, 1.7 µm

Mobile phase A 0.05 M Na-phosphate buffer pH 6.5/acetonitrile, 95/5 v/v

Mobile phase B 0.05 M Na-phosphate buffer pH 6.5/acetonitrile, 50/50 v/v

| Flow gradient | Time [min] | % B |
| --- | --- | --- |
| | 0 | 20.0 |
| | 10 | 32.0 |
| | 35 | 47.0 |
| | 36 | 20.0 |
| | 44 | 20.0 |

| | |
| --- | --- |
| Flow rate | 0.3 mL/min |
| Column temperature | 30° C. |
| Injected amount | 2 µL |
| Autosampler temperature | 5° C. |
| UV detection | 210 nm |

Preparation of 0.05 M Phosphate Buffer pH 6.5:

7.8 g sodium dihydrogen phosphate dihydrate was dissolved in approx. 900 mL purified water. pH was adjusted to 6.5 using 15% sodium hydroxide solution. Finally, the solution was filled up to 1000 mL with purified water and filtrated through a 0.22 µm membrane filter.

Preparation of Mobile Phase A:

25 mL of acetonitrile was added to 475 mL of 0.05 M phosphate buffer pH 6.5.

Preparation of Mobile Phase B:

250 mL of acetonitrile was added to 250 mL of 0.05 M phosphate buffer pH 6.5.

Preparation of Sample and Reference Solutions:

Sample and reference solution were prepared by dissolving 24 mg of CMS-Na in 1 mL purified water. Immediately after dissolution, the solution was diluted to 2 mg/mL with methanol.

Determination of Free Colistin:

Determination of free colistin was performed according to European Pharmacopeia 9.5 (July 2017:0319). The hydrazine sulfate solution, hexamethylene tetramine solution, primary opalescent suspension, standard of opalescence, and reference suspensions were prepared as in Example 2. The assay for free colistin was also prepared according to Example 2.

RP-HPLC Method for Zidovudine:

RP-HPLC chromatography for quantity and purity of zidovudine was performed according to monograph Ph. Eur. 9.5 (January 2017:1059). The following chromatographic conditions were used for the analysis.

Column XTerra RP18, 4.6×250 mm, 5 µm

XTerra RP18 VanGuard cartridge, 3.9×5 mm, 5 µm

Mobile phase A 2 g/L ammonium acetate, pH 6.8

Mobile phase B Acetonitrile

| Flow gradient | Time [min] | % B |
| --- | --- | --- |
| | 0 | 5.0 |
| | 3 | 5.0 |
| | 18 | 15.0 |
| | 28 | 70.0 |
| | 43 | 70.0 |
| | 44 | 5.0 |
| | 50 | 5.0 |

| | |
| --- | --- |
| Flow rate | 1.5 mL/min |
| Column temperature | 30° C. |
| Injected amount | 20 µL |
| Autosampler temperature | 5° C. |
| UV detection | 265 nm |

Preparation of Mobile Phase A:

Mobile phase A was prepared by dissolving 2 g ammonium acetate in 800 mL of purified water, pH was adjusted to 6.8 with acetic acid. The solution was made up to 1 L with purified water.

Preparation of Diluent:

Diluent was prepared by mixing 76 mL mobile phase A with 4 mL of ACN and 20 mL methanol.

Preparation of Sample and Reference Solutions:

Sample solution was prepared by dissolving 1 mg of zidovudine in 1 mL of diluent. Reference solution A: 2 mg of impurity C and 2 mg of impurity B were dissolved in 50 mL diluent. 1 mL of this solution was diluted with 19 mL diluent. System suitability solution: 5 mg of Zidovudine for SST (contains impurity A, impurity G and impurity H) was dissolved in 5 mL of reference solution A.

Karl Fischer Titration:

50 to 150 mg of the corresponding lyophilisate was weighed into a glass vial which was sealed with a crimp cap. The sample was transferred into the oven of the Karl Fischer coulometer (756/774; Metrohm) which was heated to 100° C. The septum of the cap was penetrated by an injection needle, and the generated water vapor was directly transferred into the titration chamber of the Karl Fischer coulometer via dry nitrogen. 2 vials per variant were examined by analyzing two samples per vial. Empty glass vials were used for blank correction.

Reconstitution Behavior

The dissolution behavior of the lyophilisates was monitored by adding 10 mL/20 mL purified water. The reconstitution process was monitored for dissolution time and behavior.

Freeze Drying Procedure:

Vials were washed with purified water. Afterwards the vials were dried and heat-treated. Stoppers were autoclaved and subsequently dried. The formulated bulk solutions were compounded according to Table 1010. CMS and Zidovudine was weighed in a beaker. Water was added. The solution was stirred at ambient temperature until complete dissolution was observed.

TABLE 10

| Aqueous based formulation | |
| --- | --- |
| Description | Amount per vial |
| CMS | 0.24 g |
| Zidovudine | 0.20 g |
| Fill volume | 20 mL |

Vials were filled with 20 mL formulated bulk solution by pipetting. Stoppers were manually placed in lyophilisation position. Product vials were placed on stainless steel racks, sealed in lyo bags and loaded into the freeze dryer. Pressure control was performed followed by the same freeze-drying cycle as in Example 2, except that primary drying was terminated after end of sublimation. After completion of the lyophilisation cycle the freeze-drying chamber was vented to 750 mbar with nitrogen, and vials were closed. After venting to atmospheric pressure vials were unloaded, capped and stored at 5° C.

Results

Residual Moisture

Table 11 gives an overview of the residual water content of the lyophilisate.

TABLE 11

| Variant | Residual moisture [%] | Standard deviation residual moisture [%] |
| --- | --- | --- |
| water | 0.52 | 0.05 |

The water samples showed a very low water content below 1.0%.

Reconstitution Behavior

A reconstitution volume of 20 mL was needed to obtain a clear solution.

Analysis of the Lyophilisates Using the Methods of the European Pharmacopeia (i) Related Substances of Zidovudine The lyophilisates of the test lyophilisation in aqueous lyo solutions were analyzed using the method for related substances of zidovudine. The obtained results are shown:

TABLE 12

| Sample | Purity/Relative peak area of zidovudine main peak [%] |
| --- | --- |
| Zidovudine Reference sample | 99.9 |
| lyophilisate | 99.8 |

The purity of zidovudine lyophilized is comparable to the reference standard. This indicates that zidovudine is stable during the lyophilisation process.

(ii) Related Substances and Composition of CMS

The lyophilisates of the test lyophilisation in aqueous lyo solutions were analyzed using the method for related substances and composition of CMS-Na. The peak pattern remained unchanged during lyophilisation.

(iii) Free Colistin in Lyophilisates

The lyophilisates of the test lyophilisation in aqueous-based systems were analyzed for free colistin. Table gives an overview of the obtained results.

TABLE 13

| Sample | Turbidity [NTU] | Acceptance criteria/ not more turbid than standard of opalescence II |
| --- | --- | --- |
| standard of opalescence II | 9.8 | — |
| Water lyophilisate sample | 15.0 | slightly |

Table 13 shows how the lyophilisate contains small amounts of free colistin, but these amounts are only slightly above the standard of opalescence II and are significantly reduced compared to the organic solvent system in Example 2. This indicates that the aqueous solvent system is improved compared to the organic solvent system and provides a useful preparation of CMS and zidovudine.

Conclusion

Surprisingly the inventors found that a combination product of CMS and zidovudine could be prepared using an aqueous solvent system, and that this solvent system was improved in terms of free colistin levels over an organic solvent system. All quality attributes of the obtained lyophilisates from the aqueous solvent system were satisfying and the free colistin assay exhibited a significant improvement over the organic solvent system.

Example 4: Lyophilisate Stability Studies

To measure the storage stability of the lyophilisate, the following protocol was carried out on the lyophilisate of Example 3.

TABLE 14

| Hold time (months) | 5° C. ± 3° C. | Storage Condition | |
|---|---|---|---|
| | | 25° C./ 60% RH | 40° C./ 75% RH |
| 3 | — | A | A |
| 6 | — | A | B |

TABLE 14-continued

| Hold time (months) | 5° C. ± 3° C. | Storage Condition | |
|---|---|---|---|
| | | 25° C./ 60% RH | 40° C./ 75% RH |
| 9 | B | B | — |
| 12 | — | A | — |

Tests at each time indicated by A included Solubility, Visible particles, Identification of Z, Assay of Z, Identification of CMS and Assay of CMS. At each time indicated by B, in addition to the attributes indicated for time-points A, the following attributes were assessed: pH, and Sterility. After 3 months at 25° C.±2° C. and 60%±5% RH, the lyophilisate was readily soluble in water with a reconstitution time of 29 seconds, and contained no visible particles. The HPLC and assay results are shown below in Tables 15-16:

TABLE 15

| | | 25° C. ± 2° C. and 60% ± 5% RH | | |
|---|---|---|---|---|
| Analysis) | Method | Target | T0 | T3 |
| Identification of zidovudine (AZT) | HPLC Ph.Eur. 2.2.29 | Retention time of main peak in test solution corresponds to retention time of reference solution | complies | complies |
| Assay of zidovudine (AZT) | HPLC Ph.Eur. 2.2.29 | 95.0-105.0% (194.8-215.3 mg/vial) | 103.6% (212.5 mg/vial) | 99.1% (203.3 mg/vial) |
| Related substances of AZT | HPLC Ph.Eur. 2.2.29 | Total impurities ≤2.0% | 0.2% | 0.3% |
| Identification of CMS | Ph.Eur. 2.2.29 | Peaks due to various, known components of CMS (e.g. CMS E1ASM8 etc) in chromatogram obtained with test solution correspond to peaks obtained in chromatogram with reference solution | complies | complies |
| Assay of CMS | Microbiological assay of antibiotics Ph.Eur. 2.7.2 | 90.0-120.0% (2,767,500-3,690,000 IU/vial) | 114.3% (3,515,912 IU/vial) | 108.2% (3,328,181 IU/vial) |
| Related substances | HPLC Ph.Eur. 2.2.29 | Peaks not related to CMS E1 or CMS E2 | 3.5% | 4.8% |

TABLE 16

| | | 40° C. ± 2° C. and 75% ± 5% RH | | |
|---|---|---|---|---|
| Analysis) | Method | Target | T0 | T3 |
| Identification of zidovudine (AZT) | HPLC Ph.Eur. 2.2.29 | Retention time of main peak in test solution corresponds to retention time of reference solution | complies | complies |
| Assay of zidovudine (AZT) | HPLC Ph.Eur. 2.2.29 | 95.0-105.0% (194.8-215.3 mg/vial) | 103.6% (212.5 mg/vial) | 98.8% (202.5 mg/vial) |
| Related substances of AZT | HPLC Ph.Eur. 2.2.29 | Total impurities 2.0% | 0.2% | 0.7% |

TABLE 16-continued

| | | 40° C. ± 2° C. and 75% ± 5% RH | | |
|---|---|---|---|---|
| Analysis) | Method | Target | T0 | T3 |
| Identification of CMS | Ph.Eur. 2.2.29 | Peaks due to various, known components of CMS (e.g. CMS E1ASM8 etc) in chromatogram obtained with test solution correspond to peaks obtained in chromatogram with reference solution | complies | complies |
| Assay of CMS | Microbiological assay of antibiotics Ph.Eur. 2.7.2 | 90.0-120.0% (2,767,500-3,690,000 IU/vial) | 114.3% (3,515,912 IU/vial) | 110.2% (3,389,418 IU/vial) |
| Related substances | HPLC Ph.Eur. 2.2.29 | Peaks not related to CMS E1 or CMS E2 | 3.5% | 5.7% |

Based on the stability data, the drug product is expected to remain within specification for at least three months at controlled room temperature (25° C.) and at accelerated conditions (40° C.).

Example 5: Infusion Stability Studies

Example 5 tests the stability of the lyophilisate following reconstitution and dilution with an infusion solution. Two infusion solutions (0.9% NaCl and 5% glucose), two storage conditions (+2 to +8° C. and +20° C. to +25° C.) and four time-points (0 h (T0), 6 h (T1), 24 h (T2), 30 h (T3)) were tested. To prepare the infusion solutions, the lyophilisate from Example 2 was first reconstituted with 20 ml of sterile water. The solution was then added to the respective infusion solution. More details are set out below.

Stability was monitored by using the microbiological assay method disclosed in co-pending application GB1910777.0. For the design of the assay, the randomized block design was used with 3 treatments of test sample and standard in each of 6 petri dishes. The evaluation of the data was carried out using Ph.Eur. 5.3 (Statistical Analysis of Results of Biological Assays and Tests) with the parallel-line model. In general, the CMS-activity in the test solutions used in the assay should be the same as the CMS-activity in the standard solutions. The microorganism for the assay was *Pseudomonas aeruginosa* ATCC 27853. The standard was colistimethate sodium CRS.

The expected activity of CMS in the obtained solution was 3,075,000 IU in 100 ml=30,750 IU/ml. The activity of CMS in solution T3 used for the microbiological assay should be 12,300 IU/ml so the infusion solution was diluted. For this dilution, a buffer solution with pH 6.0 prepared from monopotassium dihydrogen phosphate, sodium hydroxide and sterile water was used. In order to keep the same solvent for all solutions (T3, T2 and T1), the further dilution steps were carried out using the same mixture of water, infusion solution and buffer solution pH 6.0—referred to below as "serial dilution solution". More details are set out below.
Preparation of Stock and Reference/Standard Solutions To prepare a standard stock solution (SL-S), the whole content of 1 vial colistimethate sodium was completely dissolved in 2.0 ml of sterile water. The certified activity in IU/vial was 285,000 IU/vial meaning that the solution contained about 142,500 IU/ml CMS. Standard stock solution was prepared fresh for each time-point.

Standard solution S0 was prepared by mixing 0.9 mL of SL-S with 3.6 ml of the infusion solution (either 0.9% NaCl or 5% glucose). The expected activity of S0 was about 28,500 IU/ml CMS. Standard solution S3 was prepared by diluting 2.2 ml of the S0 solution to 5.0 ml using the buffer solution pH 6.0. The obtained solution S3 contained about 12,540 IU/ml CMS. Standard solution S2 was prepared by mixing 2.0 ml of solution S3 with 2.0 ml of solution for serial dilutions to obtain an expected activity of 6,270 IU/ml CMS. Standard solution S1 was prepared by mixing 2.0 ml of solution S2 with 2.0 ml of solution for serial dilutions to obtain an expected activity of 3,135 IU/ml CMS.
Preparation of the Infusion Solutions Test solution T0 was prepared by adding 20 ml sterile water to four vials containing the combination product in lyophilised form. The combination product consisted of CMS and zidovudine. After dissolution of the contents, a reconstituted solution with an expected activity of 153,750 IU/ml CMS was obtained.

20 ml of reconstituted solution was removed from each of the vials, and added to either 80 ml sterile NaCl infusion solution or 80 ml sterile 5% glucose infusion solution. The expected activity of the obtained solutions T0 was about 30,750 IU/ml CMS.

Immediately after preparation of the infusion solutions, about 10 ml was removed from each vial and used to prepare the four test solutions as described below. The other part of the infusion solutions was stored at either 2-8° C. or 20-25° C. After 6, 24 and 30 hours following preparation of the infusion solutions, about 10 ml was removed from the stored solutions and used to prepare the test solutions as described below.
Preparation of Test Solutions for the Combination Product 4.0 ml of each of the four T0 solutions (or of the solutions sampled after 6, 24 or 30 hours) was diluted to 10.0 ml using buffer solution pH 6.0. The expected activity of the obtained solution T3 was about 12,300 IU/ml CMS.

Solution T2 was prepared by mixing 3.0 ml of solution T3 with 3.0 ml solution for serial dilutions to obtain a solution with an expected activity of about 6,150 IU/ml. Solution T1 was prepared by mixing 2.0 ml of solution T2 with 2.0 ml of solution for serial dilutions to obtain a solution with an expected activity of about 3,075 IU/ml.
Preparation of the Inoculum of the Test Micro-Organism 100 µl of *P. aeruginosa* ATCC 27853 glycerol stock was inoculated in 5 ml Caso Broth and incubated overnight at 30-35° C. for 18 to 24 hours. The microbial count of the overnight culture was identified using a pour plate method: a 10-fold dilution series was prepared from the overnight culture, and from these dilutions, $10^{-6}$ and $10^{-7}$ 100 µl were taken and each placed into a sterile Petri dish. Molten cooled agar was poured into the Petri dish and mixed. After solidification of the agar, the plates were inverted and incubated at 30-35° C. for 24 to 72 hours. In the meantime, the overnight culture was stored at 2 to 8° C. After incubation, microbial count was determined and inoculum with microbial count around $1 \times 10^7$ CFU/ml was prepared from the overnight culture.

Preparation of Agar Plates

Two time-points (0 and 6 hours as well as 24 and 30 hours), two infusion solutions (0.9% NaCl and glucose, respectively for each test point) and two incubation temperatures (2-8° C. and 20-25° C., for each test point and infusion solutions) were tested per day. For each condition, 6 plates (Ø14.5 cm) were required; this totaled 48 plates per day (96 plates for the whole test).

Culture Medium Caso-Agar was prepared as known in the art. The flasks with the solid culture were liquefied and tempered at 45-55° C. 2 ml of the inoculum (about $1 \times 10^7$ CFU/ml) of *P. aeruginosa* was pipetted into each of the flasks of tempered culture medium and mixed thoroughly. For the preparation of the agar plates, 57 ml of liquefied and inoculated culture medium was measured and transferred into each of the 48 petri dishes. All plates were stood exactly horizontal for at least 1 hour at room temperature to allow the agar to solidify. Using a sterile biopsy punch, 7 cavities with a diameter of 6 mm were prepared in each of the 48 agar plates, and the plates stored at 2 to 8° C. until the next day.

Procedure

For each time-point (including 0 h) 50 µl of the sample solutions T1, T2 and T3 as well as 50 µl of the standard solutions S1, S2 and S3 were pipetted into the cavities of each of the 24 agar plates. In the middle cavity of each plate, 50 µl of buffer solution was pipetted. For pre-diffusion, the plates were stood exactly horizontal for 3 hours at room temperature. All agar plates were then incubated at 30° C. to 35° C. for around 18 hours. After incubation, the inhibition zones were measured in mm to the nearest 0.1 mm and evaluated according to Ph.Eur. 5.3.

Results

The calculation of the microbiological activity of the sample was carried out based on the statistical analysis of results of biological assays set out in Ph.Eur. 5.3 using the parallel-line model and randomized block design of the assay. These results are shown in Tables 17 to 20 below to three significant figures:

TABLE 17

| Time | Infusion Solution | Storage condition | Potency MIU/vial | Potency IU/mg |
|---|---|---|---|---|
| 0 h | 0.9% NaCl | 5° ± 3° C. | 3.21 | 13,000 |
| 6 h | 0.9% NaCl | 5° ± 3° C. | 3.38 | 13,700 |
| 24 h | 0.9% NaCl | 5° ± 3° C. | 3.13 | 12,700 |
| 30 h | 0.9% NaCl | 5° ± 3° C. | 3.42 | 13,900 |

TABLE 18

| Time | Infusion Solution | Storage condition | Potency MIU/vial | Potency IU/mg |
|---|---|---|---|---|
| 0 h | 0.9% NaCl | RT (Room Temperature) | 3.24 | 13,200 |
| 6 h | 0.9% NaCl | RT (Room Temperature) | 3.52 | 14,300 |
| 24 h | 0.9% NaCl | RT (Room Temperature) | 3.78 | 15,400 |
| 30 h | 0.9% NaCl | RT (Room Temperature) | 4.03 | 16,400 |

TABLE 19

| Time | Infusion Solution | Storage condition | Potency MIU/vial | Potency IU/mg |
|---|---|---|---|---|
| 0 h | 5% Glucose | 5° ± 3° C. | 3.21 | 13,000 |
| 6 h | 5% Glucose | 5° ± 3° C. | 3.45 | 14,000 |
| 24 h | 5% Glucose | 5° ± 3° C. | 3.45 | 14,000 |
| 30 h | 5% Glucose | 5° ± 3° C. | 3.53 | 14,300 |

TABLE 20

| Time | Infusion Solution | Storage condition | Potency MIU/vial | Potency IU/mg |
|---|---|---|---|---|
| 0 h | 5% Glucose | RT (Room Temperature) | 3.24 | 13,200 |
| 6 h | 5% Glucose | RT (Room Temperature) | 3.40 | 13,800 |
| 24 h | 5% Glucose | RT (Room Temperature) | 3.83 | 15,600 |
| 30 h | 5% Glucose | RT (Room Temperature) | 4.15 | 16,900 |

These results show that all solutions whether refrigerated or at room temperature, were stable for up to 6 hours. The refrigerated solutions were also stable for up to 30 hours. The room temperature samples were stable up to 24 hours. This stability is comparable with CMS alone and means that infusion solutions should be provided with instructions to store for no more than 6 hours at room temperature conditions and 24 hours at refrigerated conditions.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

ABBREVIATIONS

ACN acetonitrile
ARB antibiotic resistance breaker
API active pharmaceutical ingredient
BDS bulk drug substance
CMC critical micelle concentration
CMS colistimethate sodium
C CMS/colistimethate sodium
DP drug product
DS drug substance
EMA European medicine agency
HPLC high performance liquid chromatography
HS-GC head-space gas chromatograph
HPLC high performance liquid chromatography
LC-MS liquid chromatography—mass spectrometry
RP-HPLC reversed-phase high performance liquid chromatography RT retention time
SD standard deviation
TBA tert-butanol
TFA trifluoroacetic acid
USP United States Pharmacopeia
Z Zidovudine

What is claimed is:

1. A pharmaceutical product comprising:
   i) a polymyxin that is colistin methane sulfonate or a pharmaceutically acceptable salt thereof;
   ii) zidovudine or a pharmaceutically acceptable salt thereof; and
   iii) optionally one or more of a buffering agent,
   wherein the pharmaceutical product is formulated as a storage stable lyophilizate.

2. The pharmaceutical product of claim 1, wherein the storage stable lyophilizate consists of the polymyxin and the zidovudine.

3. The pharmaceutical product of claim 1, wherein the polymyxin is colistin methane sulfonate sodium.

4. The pharmaceutical product of claim 1, wherein the polymyxin is present in an amount between about 0.5 MIU and about 14 MIU.

5. The pharmaceutical product of claim 1, wherein the zidovudine is present in a therapeutically effective amount of between about 50 mg and about 1500 mg.

6. The pharmaceutical product of claim 1, wherein the polymyxin is present in an amount, the zidovudine is present in a therapeutically effective amount, and the amount of polymyxin is greater than the therapeutically effective amount of zidovudine, on a % w/w basis.

7. The pharmaceutical product of claim 6, wherein the weight ratio of polymyxin to zidovudine is between about 8:1 to about 11:10.

8. The pharmaceutical product of claim 1, for use in treating a gram-negative bacterial infection.

9. The pharmaceutical product for use of claim 8, wherein the gram-negative bacterial infection is caused by *Enterobacteriaceae, Enterobacter, Pseudomonas*, or *Acinetobacter*.

10. The pharmaceutical product for use of claim 8, wherein the gram-negative bacterial infection is caused by a (multi)-drug-resistant strain of bacteria.

11. A sealed vial containing the pharmaceutical product of claim 1.

12. The pharmaceutical product of claim 1, wherein the therapeutically effective amount of zidovudine is between about 150 mg and about 500 mg.

13. The pharmaceutical product of claim 1, wherein the amount of the polymyxin is between about 40 mg and about 400 mg.

14. A method of treating a gram-negative bacterial infection comprising administering an effective amount of the pharmaceutical product of claim 1 to a subject in need thereof.

15. The method of claim 14, wherein the gram-negative bacterial infection is caused by *Enterobacteriaceae, Enterobacter, Pseudomonas*, or *Acinetobacter*.

16. The method of claim 14, wherein the gram-negative bacterial infections is caused by a (multi)-drug-resistant strain of bacteria.

17. A process for preparing the pharmaceutical product of claim 1, wherein the process comprises: mixing a therapeutically effective amount of the polymyxin, a therapeutically effective amount of zidovudine or the pharmaceutically acceptable salt thereof, and an aqueous carrier, to form a sterile solution, sterile filtering the solution, filling a vial with the filtered solution, and subjecting the filled vial to lyophilization.

18. The process of claim 17, wherein the polymyxin is colistin methane sulfonate sodium.

19. The process of claim 17, wherein the fill volume per vial is between about 10 ml and about 20 ml.

* * * * *